United States Patent
Birthisel et al.

(10) Patent No.: US 8,969,250 B2
(45) Date of Patent: Mar. 3, 2015

(54) DISPERSIBLE ADHESIVE GRANULES

(75) Inventors: Timothy D. Birthisel, Perrysburg, OH (US); Joe Schumski, IV, Luckey, OH (US)

(73) Assignee: The Andersons, Inc., Maumee, OH (US)

( * ) Notice: Subject to any disclaimer, the term of this patent is extended or adjusted under 35 U.S.C. 154(b) by 496 days.

(21) Appl. No.: 12/956,930

(22) Filed: Nov. 30, 2010

(65) Prior Publication Data

US 2011/0130291 A1 Jun. 2, 2011

Related U.S. Application Data

(60) Provisional application No. 61/265,063, filed on Nov. 30, 2009.

(51) Int. Cl.

| | |
|---|---|
| A01N 25/26 | (2006.01) |
| A01P 3/00 | (2006.01) |
| A01P 7/04 | (2006.01) |
| A01P 13/00 | (2006.01) |
| A01P 21/00 | (2006.01) |
| A01P 23/00 | (2006.01) |
| A01N 25/12 | (2006.01) |
| A01N 47/38 | (2006.01) |

(52) U.S. Cl.
CPC ............... *A01N 25/12* (2013.01); *A01N 47/38* (2013.01)

USPC ........ 504/367; 504/116.1; 504/118; 504/358; 504/360; 504/361

(58) Field of Classification Search
None
See application file for complete search history.

(56) References Cited

U.S. PATENT DOCUMENTS

| 3,560,616 A | * | 2/1971 | Schaffer | .................. 514/249 |
| 2007/0280981 A1 | * | 12/2007 | Birthisel | .................. 424/405 |

FOREIGN PATENT DOCUMENTS

| WO | WO 2004066730 A1 | * | 8/2004 |
| WO | WO 2007112339 A2 | * | 10/2007 |

* cited by examiner

*Primary Examiner* — Abigail Fisher
*Assistant Examiner* — Frank Choi
(74) *Attorney, Agent, or Firm* — Blue Filament Law PLLC; Avery N. Goldstein

(57) ABSTRACT

A process for treating foliage by retaining an active agent in contact with the foliage is provided that includes the application of a biologically active ingredient carrier granule. The granule includes a mineral component, a cellulosic component, and a binder flowing upon wetting intermixed with the mineral component and the cellulosic components. A biologically active ingredient is added to the granule to treat the foliage. The foliage in either a dry or pre-wetted state. The contact of the granule with water causes the granule to flow to form a coherent film bound by the binder on the foliage with the active agent retained in the film in contact with the foliage.

18 Claims, 2 Drawing Sheets

Figure 1C:
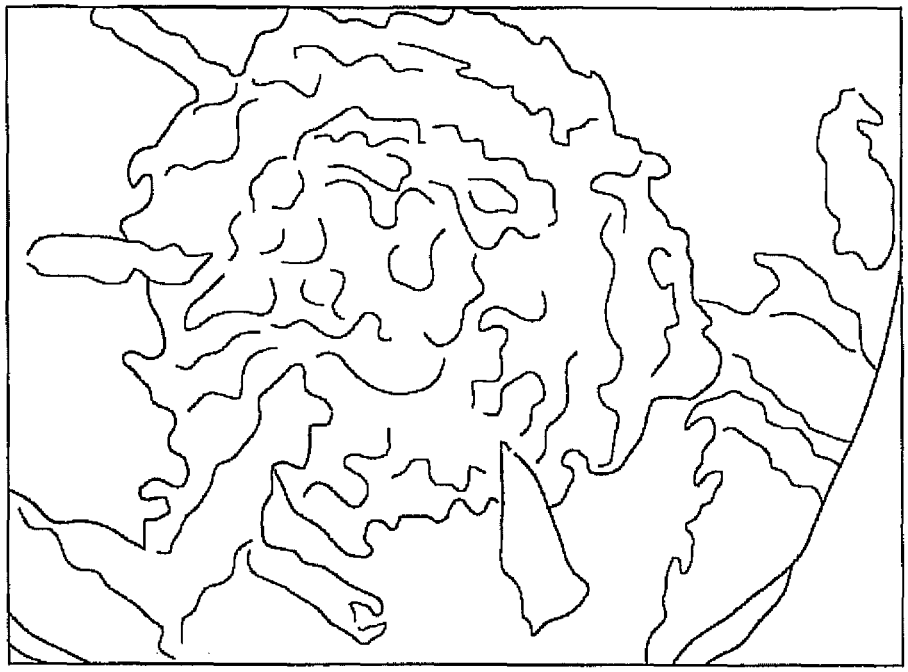

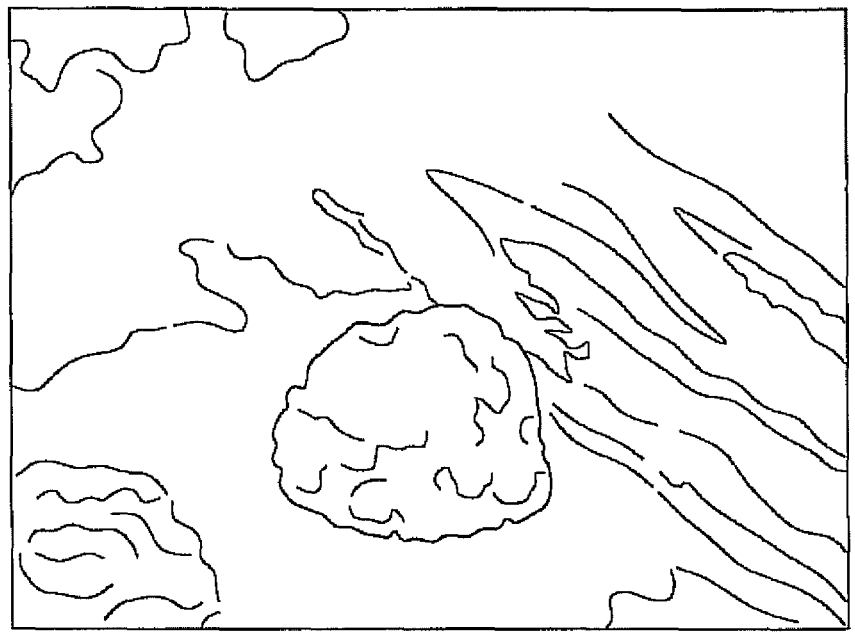
FIG. 1A  t=0 sec
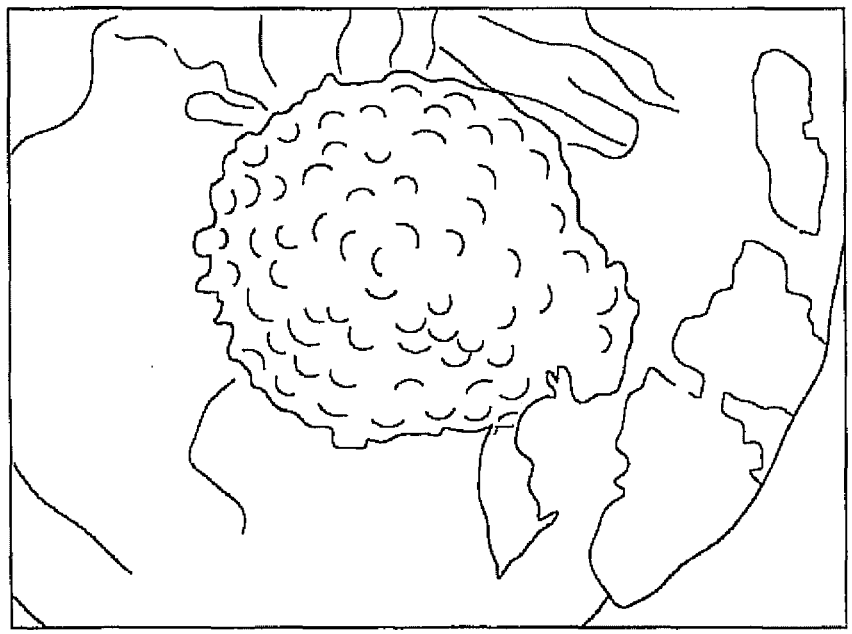
FIG. 1B  t=2 sec

DISPERSIBLE ADHESIVE GRANULES

RELATED APPLICATIONS

This application is a non-provisional application that claims priority benefit of U.S. Provisional Application 61/265,063 filed Nov. 30, 2009; the contents of which are hereby incorporated by reference.

FIELD OF THE INVENTION

The present invention in general relates to a biologically active ingredient granule and in particular to a biologically active ingredient granule that is adherent to desired plant species.

FIELD OF THE INVENTION

The present invention in general relates to a biologically active ingredient granule and in particular to a biologically active ingredient granule that is adherent to desired plant species.

BACKGROUND OF THE INVENTION

Biologically active ingredients are widely used in agriculture, landscape and turf management to kill or regulate the growth of desired or unwanted plants, diseases, insects or other pests and/or to nourish, protect, regulate the growth, or enhance the appearance of desired plants, and/or to modify the behavior of animals interacting with plants. In the course of a growing season, modern plant culture may dictate multiple treatments with biologically active ingredients. A practitioner of plant culture must decide whether a particular treatment is best performed with a granular product or a liquid spray application. Crops as diverse as turf, grain crops, tubers, ground fruits and vegetables, orchard crops, and horticultural plantings are routinely treated with either granular or sprayed substances. Each application method has limitations. Specifically, while granular herbicide tends to provide a simple broadcast, generally long-term release, accurate placement of product in the treated area, relative freedom from spills and other environmental releases, and safer handling, granules are difficult to adhere to plant surfaces.

In contrast, spray treatment generally requires considerable skill for application, may contact only exposed foliage, and may tend to dissipate, or "run off," quickly. Spray treatment also has the undesirable attribute of spray drift that contaminates surrounding areas with active agent intended for crop application. In spite of the difficulties associated with liquid application, the improved adherence properties of liquid spray of biologically active materials targeting weed leaves or foliage make this a desirable route of delivery.

Regardless of whether spray or granule broadcast is used, the application method is not completely satisfactory. For instance, spray application is quickly dissipated and leached into soil by rain. Granular formulations often require the use of additional herbicide due to inefficiencies in the timely release, or inefficient environmental extraction of the herbicide from the associated granular substrate materials.

Thus, there exists a need for a carrier granule carrying a biologically active ingredient, the carrier adhering to the surface of plants, grasses and weeds using a granule that disperses rapidly when applied to wetted foliage, dries quickly, and forms a film on a target that retains a biologically active agent to the contacted foliage.

SUMMARY OF THE INVENTION

A process for treating foliage by retaining an active agent in contact with the foliage is provided that includes the application of a biologically active ingredient carrier granule. The granule includes a mineral component, a cellulosic component, and a binder flowing upon wetting intermixed with the mineral component and the cellulosic components, A biologically active ingredient is added to the granule to treat the foliage. The foliage in either a dry or pre-wetted state. The contact of the granule with water causes the granule to flow to form a coherent film bound by the binder on the foliage with the active agent retained in the film in contact with the foliage.

BRIEF DESCRIPTION OF THE DRAWINGS

FIGS. 1A-D depict a progressive sequence of an inventive granule change when contacted with water.

DETAILED DESCRIPTION OF THE PREFERRED EMBODIMENTS

The present invention has utility as a granule to deliver a biologically active ingredient to plant culture. Adherence of an inventive granule to a plant surface occurs with controlled granule size and density to restrict drift and promote retention on a target, along with water from precipitation, irrigation, dew, co-application with the granules from special application equipment, or guttation water from the plant itself. An inventive granule, upon contact with a moistened plant surface or upon co-application with moisture, disperses on the plant surface to facilitate the distribution and retention of the biologically active ingredient to the plant leaf and stalk.

An inventive granule retains its size and shape during handling and application to a desired area and adheres to moistened plant surfaces when the granule comes into contact with the plant. Thus, the durability of the particle affords both ease of application and adherence of the granule on a desired site of action when sufficient moisture is present to wet the granule surface, facilitating distribution and retention of biologically active ingredients to a target. Often without the presence of added water from rain or irrigation, the moisture present on a plant surface such as from ambient humidity or natural plant moisture is often sufficient to activate the adherent properties of the inventive granule.

A granule is preferably sized such that it is applicable to a target area with minimal drift yet is not too large that the adherent properties are thwarted by excessive size and density. As such, the size, such as diameter, and density of an inventive granule are critical features of an inventive granule.

Typically, a granule has a diameter from 10 to 500 microns. More preferably, a granule has a diameter from 50 to 250 microns. In a most preferred embodiment, an inventive granule has a diameter of 100 to 150 microns. Alternatively, 90% of the particles have a diameter less than 150 microns.

An inventive granule includes a mineral component. Preferably, a mineral component has greater density than a cellulosic component. In a preferred embodiment a mineral component has a density from about 0.8 to 3 $g/cm^3$. Suitable mineral components illustratively include rock dust, stones, clays, specific examples of which include limestone particulate, powdered dolomite, dolomitic limestone, gypsum, and pelletized lime. A mineral component is typically present in a granule according to the present invention in an amount from 10 to 90 total weight percent of the granule.

An inventive granule further includes a cellulosic material with a particle density less than the density of the mineral component. The particle density of the cellulosic component is preferably from about 0.05 to 1 g/cm$^3$. More preferably, a cellulosic component has a density from about 0.08 to 0.6 g/cm$^3$. Cellulosic materials operative herein illustratively include grain hulls, peanut hulls, corncob, cereal, plant pulp, wood dust, and dried distillers grain (DDG), bait particulate, and other plant-based cellulosic materials. The cellulosic granule component is readily formed through conventional techniques such as grinding and sieving, extrusion pelletization and sieving, and related techniques well known to the art. While it is appreciated that the cellulosic granules operative herein are optionally formed by aggregating smaller cellulosic fragments, in a preferred embodiment the cellulosic granules are monolithic. Cellulosic granules are typically present in a granule according to the present invention in an amount from 10 to 90 total weight percent of the granule.

The inventive combination of mineral component of comparatively higher density and optionally larger mean particle size relative to cellulosic component with a lower density and optionally smaller mean particle size provides for a larger dispersion volume relative to mineral-based granular materials as detailed in U.S. Pat. No. 6,231,660 or 6,613,138, the contents of each are incorporated herein by reference. More preferably, the relative ratio of the mineral component and the cellulosic component promotes a particle with a density sufficient to resist drift during broadcast yet is not so heavy as to fail to adhere to a target due to gravitational and inertial forces during application.

In a preferred embodiment, the weight percent ratio of the mineral component and the cellulosic component yield a granule with a density from about 0.01 to 2 g/$cm^3$. More preferably, the granule has a density from about 0.05 to 1.5 g/$cm^3$. In a most preferred embodiment the inventive granule has a density from about 0.08 to 1.2 g/$cm^3$.

The inclusion of cellulosic component according to the present invention allows product total density to be adjusted to facilitate bag filling. Additional advantages achieved through the inventive combination include less mineral component fragmentation during transport and as a result less product dusting during application. Still a further advantage includes a larger volume of material to be applied by the end user so as to favor lower active agent dispersion density per area of vegetation so as to reduce overall active agent usage. It is appreciated that conventional spreaders of granulated products provide limited end user control over spreading density; adjustment of delivery medium according to the present invention is readily tailored to lessen over usage of active agents. A still further attribute of the inventive granule is water absorption by cellulosic material that in turn facilitates prolonged granule wetting and dispersion into a film on a target plant.

A binder component is preferably present in a granule in an amount ranging from 0.1% to 75% by weight of the total dry weight of the granule. A binder component is included in a particle as necessary to produce or promote cohesion in forming a particle capable of retaining a specified form during transport and/or distribution. A binder component illustratively includes bentonite clay, carbohydrate, protein, lipid, synthetic polymer, glycolipid, glycoprotein, lipoprotein, lignin, a lignin derivative, a carbohydrate-based composition, and a combination thereof. In a preferred embodiment the binder component is a lignin derivative and is optionally calcium lignosulfonate. Alternatively, the binder component is selected from the group consisting of: a monosaccharide, a disaccharide, an oligosaccharide, a polysaccharide and combinations thereof. Specific carbohydrate binders illustratively include glucose, mannose, fructose, galactose, sucrose, lactose, maltose, xylose, arabinose, trehalose and mixtures thereof such as corn syrup; celluloses such as carboxymethylcellulose, ethylcellulose, hydroxyethylcellulose, hydroxymethylethylcellulose, hydroxyethylpropylcellulose, methylhydroxyethyl-cellulose, methylcellulose; starches such as amylose, seagel, starch acetates, starch hydroxyethyl ethers, ionic starches, long-chain alkyl starches, dextrins, amine starches, phosphates starches, and dialdehyde starches; plant starches such as corn starch and potato starch; other carbohydrates such as pectin, amylopectin, xylan, glycogen, agar, alginic acid, phycocolloids, chitin, gum arabic, guar gum, gum karaya, gum tragacanth and locust bean gum; vegetable oils such as corn, soybean, peanut, canola, olive and cotton seed; complex organic substances such as lignin and nitrolignin; derivatives of lignin such as lignosulfonate salts illustratively including calcium lignosulfonate and sodium lignosulfonate and complex carbohydrate-based compositions containing organic and inorganic ingredients such as molasses. Suitable protein binders illustratively include soy extract, zein, protamine, collagen, and casein. Binders operative herein also include synthetic organic polymers capable of promoting or producing cohesion of particle components and such binders illustratively include ethylene oxide polymers, polyacrylamides, polyacrylates, polyvinyl pyrrolidone, polyethylene glycol, polyvinyl alcohol, polyvinylmethyl ether, polyvinyl acrylates, polylactic acid, and latex. In a preferred embodiment, the binder is calcium lignosulfonate, molasses, a liquid corn starch, a liquid corn syrup or a combination thereof.

Upon forming either of the mineral component or the cellulosic component, a formulation of an active agent is applied to the granules. It is appreciated that one can: apply one or more liquid active agents to the mineral component and separately apply one or more liquid active agents to the cellulosic component, or alternatively, mix the mineral component and the cellulosic component in a predetermined ratio with the binder and thereafter apply one or more active agents to the intermixed components or finished granules. Preferably, the active agent is dissolved in a solvent and applied to the preformed mineral component, cellulosic component, or a combination thereof. Alternatively, it is appreciated that a liquid active agent formulation is incorporated into a binder solution during the formation of a granule An active agent in powder form is intermixed with mineral component and cellulosic component to form the inventive delivery granule. The active agent granules are preferably of a mean size less than 20 percent that of the mean mineral component size. Without intending to be bound to a particular theory, electrostatic forces are believed to be operative to retain active agent powder in contact with the components of an inventive granule.

An active agent powder is alternatively adhered to an inventive granule surface through resort to a surface tackifier. The tackifier coating makes the surface sticky to adhere the powder distinct from the binder that is encompassed largely within the aggregated granule core. Preferably, active agent powder is sized such that the powder grain diameter has a mean particle diameter of less than 10% that of the mineral component mean size. More preferably, the active agent powder has a mean diameter of less than 2% that of the mineral component particle diameter. Effectively, any conventional active agent powder is operative within the present invention.

A plasticizer is optionally added during or after the formation of a granule. By virtue of the inclusion of impregnated plasticizer according to the invention, the resulting granules are well suited to readily absorb substantial and repeated impacts, shears, or compressions. The plasticizer-containing granule tends to deform while maintaining its integrity, increasing the attritional forces the inventive granule can absorb before reaching a point of catastrophic failure. The amount of fragments or dust formed as a result of such mechanical attrition is also reduced. A plasticizer, such as glycerol, when introduced, results in the plasticizer being absorbed into the interior of the granule and incorporated into the granule without resulting in agglomeration.

When the plasticizer is introduced as a post-formation granule coating, the plasticizer provides to reformulate a granule to increase mechanical robustness. It is noted that the process of converting mechanically sensitive granules to mechanically robust granules does not diminish desirable properties such as ease of production, handling, solubility, enzymatic stability, thermal stability, and resistance to water pickup during storage in humid conditions.

Suitable plasticizers which are incorporated into the granule are nonvolatile solvents which reduce the brittleness and enhance deformability of the granule. Typically plasticizers are low molecular weight organic compounds generally with molecular weights between 50 and 1000. Examples include, but are not limited to, polyols (polyhydric alcohols), for example alcohols with many hydroxyl groups such as glycerol, glycerin, ethylene glycol, diethylene glycol, triethylene glycol, propylene glycol, dipropylene glycol, polyethylene glycol; polar low molecular weight organic compounds, such as urea, sugars, sugar alcohols, oxa diacids, diglycolic acids; and other linear carboxylic acids with at least one ether group, $C_1$-$C_{12}$ dialkyl phthalates. Other plasticizers operative herein illustratively include ethanolacetamide; ethanolformamide; triethanolamines such as triethanolamine acetate; thiocyanates, such as sodium and ammonium thiocyanates. Most preferred as plasticizers are glycerol, triethylene glycol, propylene glycol, sorbitol, and polyethylene glycol having an average molecular weight below about 600. Generally, the ratio of plasticizer to polymer ranges from about 0.05 to about 5.0. The plasticizer is preferably present at a level of about 0.05 to about 25% by weight of total dry weight of the granule, preferably about 1 to 10% by weight of total dry weight of the granule; and more preferably about 1.5 to about 5.0% by weight of total dry weight of the granule. The exact level depends on factors such as plasticizer identity, granule size, and plasticizer tack.

Figure 1D:
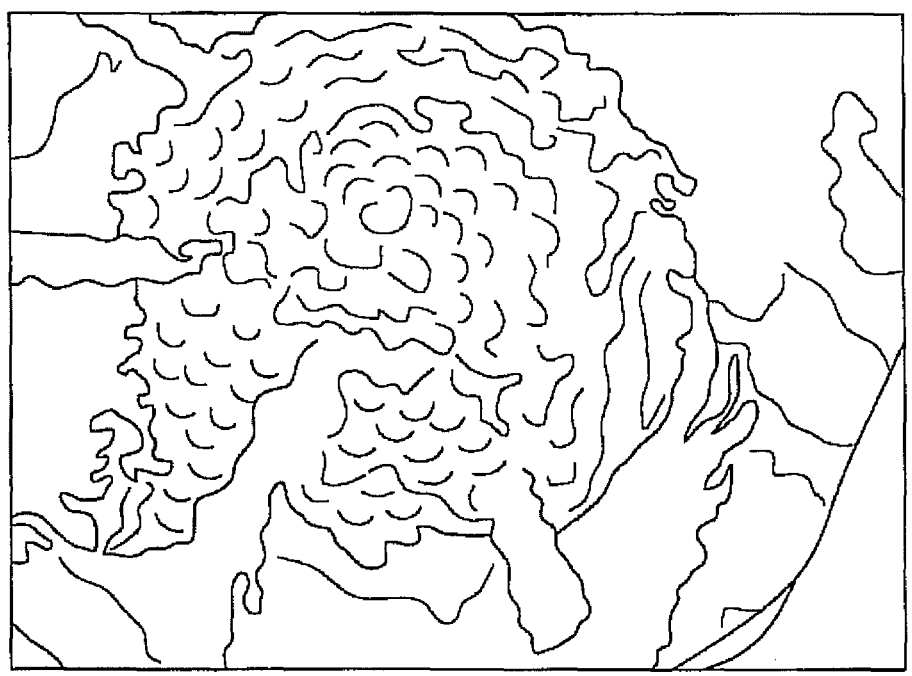

In one embodiment, an inventive granule disperses by breaking up into greater than 100 smaller pieces upon contact with water over a period of time ranging from 1 second to 24 hours. Preferably, an inventive granule disperses into 1,000 to 10,000 smaller pieces over a period of time ranging from 1 second to 12 hours. Even more preferably, a granule disperses into 100 to 10,000 smaller pieces over a period of 30 seconds to 6 hours. Most preferably, an inventive granule disperses as described over a period of 5 seconds to 5 minutes. The swelling and dispersion of an inventive granule is depicted graphically in FIGS. 1A-1D as renderings derived from video imagery. FIG. 1A depicts a dry granule (t=0 sec), while FIGS. 1B-1D depict swelling and dispersion at times of 2, 4, and 6 seconds, respectively.

In a preferred embodiment, a granule becomes flowable upon contact with water to form a coherent film on a target. A film is typically circular when a target is horizontal and substantially flat. Typically, a film has a diameter between 0.1 and 100 times the diameter of the inventive granule prior to flattening and spread flowing. Preferably, a film has a diameter of 1 micron to 5 microns. It is appreciated that an inventive film is produced upon flow of the inventive granule that is elongate in shape such as formation of a film during gravitational movement of an inventive granule during dispersion or a film is an irregular shape dictated by the shape of the target upon which dispersion occurs and as the result of gravitational, wind, or other forces. In a preferred embodiment a granule disperses in between 1 second to 24 hours. More preferably, dispersion occurs between 1 minute and 1 hour. Most preferably, dispersion occurs in less than one minute.

Without intending to be bound to a particular theory, an inventive granule contains a binder that is suspendable or soluble in water and upon granule wetting, a granule binder softens carrying constituent material and cellulosic particulate therewith. Dynamically, a granule on foliage upon wetting flattens in height and is observed to spread in two dimensions on the foliage surface, the particular constituents and the active agent being retained as a coherent film by a matrix of binder.

The ability of the inventive material to flow with water is generally measured in a water dispersibility test. The test involves placing about 10 grams of the inventive granules into 100 ml of water at room temperature in a closed glass container. The container is then inverted and the time is observed until the material disperses. After every minute, the container is inverted. The inventive granules have a dispersibility time of generally less than 15 minutes with a period of less than 5 minutes being preferred and a period of less than 2 minutes being most preferred. The inventive particle provides delivery system active agents illustratively including plant nutrients, pesticides, hormones, herbicides, micronutrients, fungicides and other active ingredients.

Water-dispersible polymers are optionally coated onto inventive granules. Water-dispersible polymers optionally function to break up an inventive granule into fine particles of no greater than about 50 microns at room temperature within about 10 minutes of moderate agitation in deionized water or a solution of less than about 5% of a detergent or nonionic surfactant. Moderate agitation is applied through the use of a stir bar at a speed in the range of 100 to 300 rpm. The water-dispersible polymer is at least suspendable in water and preferably has a solubility of at least 1% by total solution weight, more preferably at least 5% in deionized water at room temperature.

The water-dispersible polymers optionally present in an inventive granule preferably have a molecular weight of more than 1,500 and are water soluble or at least water suspendable. The water-dispersible polymers illustratively include polyvinyl alcohols (PVA), polyethylene glycols (PEG), polyethylene oxides (PEO), polyvinyl pyrrolidones (PVP), cellulose ethers, alginates, gelatin, modified starches and substituted derivatives, hydrolysates and copolymers thereof. Most preferred polymers are PVA, cellulose ethers, such as methyl cellulose and hydroxylpropyl cellulose, gelatin and modified starches, such as hydroxypropyl starch produced from cornstarch. Mostly preferred is PVA. The polymers are optionally utilized in a foamed morphology. If PVA is used, in a preferred embodiment the polymer has a level of hydrolysis in the range of about 50 to 99%, at least about 80%, at least about 85%, at least about 90%, and at least about 95%. The polymer may have an average molecular weight of about 4,000 to 250,000, preferably from 5,000 to 200,000; also from 10,000 to 100,000. The polymer generally constitutes about 0.05% to about 10% total weight of the granule.

The granule preferably incorporates a biologically active ingredient (BAI) therein or coated on the carrier particle surface. The BAI is present in an amount ranging from 0.05% to 50% by weight of the total dry weight of the granule. The BAI incorporated with the granule illustratively include herbicides, insecticides, fungicides, plant growth regulators, pest reproductive control agent, other pesticides, macro (or primary) plant nutrients, secondary plant nutrients, micronutrients, biostimulants, or protective/coloring agents used to coat or alter the appearance of plant surfaces for agronomic or aesthetic purposes, as well as other protectant and enhancing materials. It is appreciated that proteinaceous and microbial active agents such as *B. thuringiensis* bacteria and proteins.

Herbicides, for purposes of this invention, include a wide array of, chemical and biological compositions which include materials in the functional, or mode of action categories of desiccants, defoliants, abscission agents, algaecides, moss control agents (silvicides), acetyl coenzyme A carboxylase inhibitors, acetolactate synthase enzyme inhibitors, synthetic auxins (action like indoleacetic acid), inhibition of auxin transport, inhibitors of photosynthesis at photosystem II Site A and others with different binding behavior, inhibition of DHP (dihydropteroate) synthase, inhibition of acetyl CoAcarboxylase (ACCase), inhibition of lipid synthesis (not ACCase inhibition), inhibitors of 5-enolpyruvylshikimate-3-phosphate (EPSP) synthase or EPSPS inhibitor, inhibition of 4-hydroxyphenyl-pyruvate-dioxygenase (4-HPPD) (bleaching), inhibitors of glutamine synthetase, inhibitors of carotenoid biosynthesis, inhibition of carotenoid biosynthesis at the phytoene desaturase step (PDS) (bleaching), inhibition of all diterpenes, inhibitors of protoporphyrinogen oxidase (PPO), inhibitors of dihydropteroate (DHP) synthase step, inhibitors of indoleacetic acid action, inhibitors of cell wall (cellulose) synthesis, Site A inhibitors of cell wall synthesis, Site B photo system I-electron diverters, inhibition of photosynthesis at photosystem 11, inhibitors of mitosis, uncoupling membrane disruptors, inhibition of 4-hydroxyphenyl-pyruvatedioxygenase (4-HPPD), enolpynivylshikimate 3-phosphate synthase enzyme inhibitors, synthetic auxins, uncoupling (membrane disruption), inhibition of VLCFAs (inhibition of cell division), inhibition of mitosis/microtubule organization, microtubule assembly inhibition, and other, unknown mechanisms. Biological, or biorational, herbicides with application to this invention fall generally into the categories of bacteria, fungi, viruses, and plants, including the spore and other reproductive forms thereof, extracts derived therefrom, and including naturally occurring and genetically engineered forms.

More particularly, herbicides commonly fall into one (or more, in the case of mixtures) of the following chemical families: aryloxyphenoxy propionates, arylaminopropionic acid, arsenicals, cineole (such as cinmethylin), cyclohexanediones, sulfonylureas, imidazolinones, pyrimidinylthiobenzoate, triazolopyrimidine, dinitroanilines, pyridazine, phenoxys (or phenoxies), benzoic acids, carboxylic acids (such as DCPA, clopyralid, trichloroacetic acid, and flouroxypyr), quinoline carboxylic acid, semicarbazone, triazines, triazinones, uracils, pyridazinone, phenyl-carbamates, nitriles, benzothiadiazoles, organoarsenicals, phenylpyridazine, ureas and substituted ureas (such as diuron, linuron, siduron, tebuthiuron, dymron, etc.), amide (such as propanil and bromobutide), thiocarbamates, organophosphates (such as bensulide), pyrazolium (such as difenzoquat), phosphoric acid compounds (such as glufosinate-ammonium and glyphosate), triazole, pyridazinone, nicotinanilide, pyridinone (such as fluridone), isoxazolidinone, diphenylethers, N-phenylphthalimides, oxadiazole, triazolinone, chloroacetamides, oxyacetamides, carbamate (such as asulam), phthalamate, phthalamate semicarbazone, nitrile, N-phenylphthalimides, oxadiazole, triazolinone, acetamides, benzoylisoxazole, isoxazole, pyrazole, pyrazolium, triketone, and benzofuran, biological herbicides including *Puccinia canaliculata, Puccinai jacea, Xanthomonas campestris, Alternaria destruens, Colletotrichzun gloeosporioides, Denthyphion papaveraceae, Pseudomonas syringae*, including any varieties or subspecies thereof. Examples of plant extract herbicides are corn gluten meal and the allelopathic exudates of various plants.

For purpose of this invention, a pest reproductive control agent operative herein includes a pheromone, molting signaling compound or steroid that upon contact with the target pest decreases the reproductive capacity of the pest. A pest reproductive control agent is preferred over a pesticide since a reproductive control agent is specific to a species or narrower group of organisms, does not bioaccumulate, and is less detrimental to predatory or bystander organisms in the pest habitat. Additionally, a reproductive control agent is unlikely to avoid the bait due to ill health effects associated with sampling, as is often the case with a lethal pesticide.

The pest reproductive control agent includes agents such as an acaracide, an antimicrobial, a bactericide, an entomopathogen, a fungicide, a synthetic plant growth regulator such as a gibberlic acid synthesis inhibitor or promoter, an herbicide, an insecticide, a molluscicide, a nemacide, a rodenticide, a pheromone, a chemosterilant, a viricide, an imagocide, a larvicide, an ovicide, a formicide, an aphidicide, a muscacide, a culicicide, an anophelicide, an arachnidcide, and a vespacide. Preferably, an inventive bait particle containing a toxic invertebrate pesticide also contains a mammalian and/or avian ingestion repellant. More preferably, it also contains both mammalian and avian ingestion repellants to lessen the likelihood of incidental ingestion by bystander higher species. Mammalian ingestion repellants illustratively include cadaverine, butyric acid, and capsaicin. Avian repellants include artificial grape flavorant.

For purposes of this invention, plant and general disease control agents include fungicides, fungistats, antibiotics and bacteriocides of the following chemical families and functional groupings; various acetamides, sterol inhibitors or demethylase inhibitors, dicarboximides (such as iprodione), phthalides, phthalmic acids, triadiazoles, isophthalates, triazines, triconazoles, strobilurins, benzimidazoles, benzithiazoles, dithiocarbamates, carboxamides, carboxides or anilides, chlorphenyls, indolecarboxylic acids, isoxazoles, imidazoles, oxazolinediones, guanidines, diguanidines, piperidines, pyridines, sulfenamides, sulfonamides, quinolines, cyanoimidazoles, pyrazoles, pyrrolecarbonitriles, spiroketalamines, thiazoles, various chemical families of oomycete (pythium) fungicides, nitriles, chlorinated hydrocarbons, phenylpyrroles, polyoxins, pyridazinones, mycotoxins (e.g. penicillin) or other antibiotics (e.g. streptomycin, kasugamycin, blasticidin, polyoxins, validamycin, mildiomycin, and oxytetracyline), morpholines, other organic compounds such as piperalin, piperazine derivatives and tolylfluanid, bronopol, organic compound mixtures (e.g. Bacticin and harpin protein), organic acids such as cinnamic acid and its derivatives, bacteria such as *Agrobacterium radiobacter, Bacillus subtilus, Erwinia carotovora, Pseudomonas flourescens* and *P. chlorophis*, and any varieties or strains thereof, fungi such as *Candida oleophila, Fusarium, Tricoderma, Streptomyces*, and *Ampelomyces* and any species, varieties or strains thereof, and viruses such as Tomovax.

For purposes of this invention, insecticides and acaricides include fast- and slow-acting neurotoxins, insect growth regulators, crop oil, feeding suppressants and repellants, acetylcholinesterase inhibitors, gamma-aminobutyric acid (GABA)-gated chloride channel antagonists, GABA-gated chloride channel antagonists, sodium channel modulators, acetylcholine receptor agonists/antagonists, acetylcholine receptor modulators, chloride channel activators, juvenile hormone mimics, feeding disruptors, mite growth inhibitors, ovicides, reproductive inhibitors, reproductive sterilants, microbial disruptors of insect mid-gut membranes, inhibitors of oxidative phosphorylation at the site of dinitrophenol uncoupling (disrupt adenosine triphosphate (ATP) formation), uncouplers of oxidative phosphorylation (disrupt H proton gradient formation), inhibitors of magnesium-stimulated ATPase, Ecdysone agonist/disruptors (disrupts insect molting by antagonizing the insect hormone ecdysone), octopaminergic agonists, Site I and Site II electron transport inhibitors, inhibitors of chitin biosynthesis type 1—Homopteran, inhibitors of chitin biosynthesis type 2-Dipteran, desiccants, fumigants, carbamates, organophosphates, chlorinated cyclodienes, polychlorocycloalkanes, phenylpyrazoles, diphenylethanes, synthetic pyrethroids, pyrethrins, chloronicotines, (nitroguanidines), nicotine, Cartap, Bensultap, Spinosyns, Avermectin, Milbemycin, juvenile hormone analogues, Bt microbials (biological insecticide/larvicide), organotin matricides, pyrrole compound, sulfite ester matricides, substituted benzoylurea, thiadiazine, triazine, benzoic acid hydrazide, botanicals (neem oil or azadirachtin, rotenone), triazapentadiene, pyridazinone, and fatty acid soaps.

For purposes of this invention, plant growth regulators are ingredients such as trinexepac-ethyl, gibberellic acid, gibberellins, cytokinins, benzyladenine, glycines, quinolenes, phosphoric acid compounds, organic carbamates, quaternary ammonium compounds, acetamides, ethychlozate, azoles, paclobutrazol, anilides, pyradazidine, pyrimidines, napthaleneacetamide, phthalmides, phenoxies, pyrimidines, hybridizing agent, biostimulants, seaweed extracts and herbicides (typically at low use rates), phthalmides, phenoxies, organic or carboxylic acids (e.g. gamma amino butyric acid and L-glutamic acid, napthalene acetic acid, clofencoet, sintofen, nicotinic acids), and herbicides (typically at low use rates).

For purposes of this invention, other pesticides include animal and bird repellants, bitter flavors, irritants, and malodorous ingredients, molluscicides (e.g., slugs and snails), nematicides, rodenticides, defoliants, chemosterilants, plant defense boosters (harpin protein and chitosan) desiccants (may also be used as a harvest aid), and other beneficial or detrimental agents applied to plant or other surfaces.

For purposes of this invention, other protectants and beneficial ingredients include attractants, baits, herbicide safeners, antidessicants, antitranspirants, frost prevention aids, inoculants, dyes, brighteners, markers, synergists, pigments, UV protectants, antioxidants, leaf polish, pigmentation stimulants and inhibitors, surfactants, moisture retention aids, humic acids and humates, lignins and lignates, molluscicides (e.g., slugs and snails), nematicides, rodenticides, defoliants, desiccants, sticky traps, and IPM lures.

Optionally, the granule incorporates a fertilizer, soil nutrient, amendment material, or other active agent such as a biologically active ingredient (BAI), fungicide, pesticide or the like. In a granule incorporating a fertilizer, soil nutrient or amendment material, the fertilizer, soil nutrient or amendment material is present in an amount ranging from 0.05% to 50% by weight of the total dry weight of the granule. In a more preferred embodiment, the fertilizer, soil nutrient or amendment material active ingredient is present in an amount ranging from 0.1% to 30% by weight of the total dry weight of the granule. In a still more preferred embodiment, the fertilizer, soil nutrient or amendment material active ingredient is present in an amount ranging from 0.5% to 10% by weight of the total dry weight of the granule.

Fertilizers are substances containing one of the plant nutrients nitrogen, phosphate or potassium and illustratively include urea, sulfur-coated urea, isobutylidene diurea, ammonium nitrate, ammonium sulfate, ammonium phosphate, triple super phosphate, phosphoric acid, potassium sulfate, potassium nitrate, potassium metaphosphate, potassium chloride, dipotassium carbonate, potassium oxide and a combination of these. Soil nutrients illustratively include calcium, magnesium, sulfur, iron, manganese, copper, zinc; oxides thereof, salts thereof and combinations thereof. Amendment materials are natural organic products such as humic acid, blood meal, bone meal, seed meal, feather meal and soy meal; meat meal; animal waste from various animal sources; activated sludge, hydrolyzed animal hair; fish byproducts; chitin; composts; and a combination thereof.

An inventive granule is produced by a number of processes. In one particular instance of the present invention, granule components including carrier particles, biologically active ingredients, and optionally plasticizers, are wet granulated through a process of steps, including mixing of various dry components, wet massing the dry powder mixture with liquid surfactants, binders or the like, alone or with the addition of a solvent to arrive at a suitable consistency for granulating. Resulting powder mixture is compressed into a large form that is subsequently ground to a desired size. It is appreciated that dry granulation is facilitated by the addition of a pressing agent, such as a stearate salt. Upon forming a granule, a granule is optionally coated with water-dispersible polymers.

Alternatively, an inventive granule is made through a layering coating process on carrier particles. A carrier particle is optionally formed from a mineral component, a cellulosic component, or a combination thereof. Upon forming a carrier particle, a liquefied formulation of a biologically active ingredient (BAI) is applied to a carrier particle surface. Preferably, the biologically active ingredient (BAI) is dissolved in a solvent. Alternatively, it is appreciated that the liquid biological guttationally active ingredient (BAI) formulation is incorporated into a binder solution that promotes cohesion in the forming of the carrier particle with the proviso that the resulting carrier particle surface has sufficient tack to adhere moisture-activated coating powder to the surface of the resulting carrier particle.

A moisture-active coating illustratively includes gum arabic, guar gum, gum karaya, gum tragacanth, and locust bean gum. The moisture-active coating constitutes in an amount of 0.5% to 10% by weight of the total dry weight of an inventive granule. In one particular instance according to the present invention, water-dispersible polymers are combined to a moisture-active coating and the resulting mixture is sprayed onto inventive granules.

It is appreciated that the present invention affords a more efficient usage of an active agent through initial broadcast adhesion to plant foliage. Additionally, cutting of foliage so treated and allowing the clippings to remain in contact with the treatment area provides a second opportunity for adhered active agents to provide an intended action. A lesser quantity of active agent is thereby used to achieve a desired result relative to conventional active carriers and usage techniques.

EXAMPLES

Example 1

Preparation of an Active Granule

Using a pan agglomeration disk, the following components are combined and mixed: 2 kilograms of +100 and −40 mesh (0.15-0.42 mm) limestone particulate, 1.8 grams of clopyralid, 1.5 grams iprodione as a pesticide, 80 grams of calcium lignosulfonate as a binder, 60 grams of glycerol as a plasticizer. The agglomeration disk is operated and adjusted to generate carrier particles in a size ranging from 10 to 500 microns before the particles are conveyed to a fluid bed dryer where the particles are dried to contain less than 0.5% moisture by weight at a temperature of 140° Fahrenheit. The particles are then separated into various size categories using conventional gyroscopic screeners. Carrier particles with mean a size of 200 microns are fed to a blender (Forberg fluidized zone blender). The carrier particles are sprayed with a guar gum solution. After coating with the guar gum solution, the resulting granule contains guar gum of 5% by weight of the granules. It is noted that application of granules of a particular size depends on the type of plant leaf or stalk. Inventive granules have a size of 10 to 500 microns are applied to pre-moistened turf at a broadcast density of clopyralid of 0.08 kg active ingredient per hectare. Greater than 95 number % of the granules are noted to adhere to the blade and stalk surfaces.

Example 2

Carrier Granules Preparation with Active Coating

The procedure of Example 1 is repeated with the exception that the iprodione is omitted. The resulting granules perform as detailed in Example 1.

Example 3

A limestone based dense mineral component formulation is prepared substantially according to Examples 1-7 of U.S. Pat. No. 6,231,660 to yield a dense mineral component having a density of 0.99 g/cm$^3$ and an index of uniformity of between 20 and 60. Forty parts by weight of the resultant dense mineral component are mixed with 60 parts per weight of peanut hull ground to a mean size guide of 75 microns and an index of uniformity of between 20 and 60 to yield a mixture density of 0.57 g/cm$^3$. The resultant material is mixed with 0.1 parts by weight of λ-cyhalothrin. The resulting material is packaged in 50 pound bags and transported to an end use field where the material was spread with a rotary spreader. As a comparative, 1 part of λ-cyhalothrin was combined with 100 parts by weight of only dense material containing granules and as a separate comparative with 100 parts by weight of only cellulosic granules. The end user noted greater ease of spreading for the inventive combination material as relative to the comparatives with an active distribution per unit area of ground more closely aligned to target area loadings relative to the comparatives. It was also noted that a large portion of the granules disperse when contacted with rain, irrigation, or other moisture present on the target which has many benefits like increased efficacy and less risk of non-target pickup.

Example 4

The granule of Example 3 is reproduced with the replacement of the peanut hull with extruded pelletized corncob of the same mean size and distribution. Fifty parts by weight of the dense material containing granules of Example 3 are mixed with 50 parts by weight of extruded pelletized corncob to yield a material having a density of 600 g/cm$^3$. The results for this delivery medium were comparable to those for the inventive medium of Example 3.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process for treating foliage by retaining an active agent in contact with the foliage comprising:
applying a biologically active ingredient carrier granule comprising:
a mineral component;
a cellulosic component;
a binder flowing upon wetting intermixed with said mineral component and said cellulosic components;
a water-dispersible polymer coating said granule, said coating breaking up said granule into fine particles upon wetting; and
a biologically active ingredient;
to the foliage in a dry or pre-wetted state;
contacting said granule with water to cause said granule to flatten and flow to spread on the foliage surface to form a coherent film bound by said binder on the foliage with said active agent retained in said film in contact with the foliage.

2. The process of claim 1 wherein the foliage is pre-wetted or wetted simultaneous with said applying of said granule.

3. The process of claim 1 wherein the foliage is pre-wetted.

4. The process of claim 1 further comprising:
cutting the foliage to yield clippings; and
placing the clippings within a target area in need of said active agent.

5. The process of claim 1 wherein said granule disperses in less than 5 minutes.

6. The process of claim 1 wherein said granule disperses in less than 1 hour.

7. The process of claim 1 wherein said granule disperses upon contact with water in less than 6 hours.

8. The process of claim 1 wherein the carrier granule has a diameter from 10 to 500 microns.

9. The process of claim 1 wherein said mineral component is a material selected from tire group consisting of: limestone, dolomite, rock dust, and clay.

10. The process of claim 1 wherein said cellulosic component is selected from the group comprising corncob, cereal, hulls, plant pulp, and wood flour.

11. The process of claim 1 wherein said biologically active ingredient is selected from the group consisting of: herbicide, insecticide, fungicide, plant growth regulator, pest reproductive control agent, pesticide, and combinations thereof.

12. The process of claim 1 wherein said carrier particle further comprises a plasticizer in an amount ranging from 1 to 10 total weight percent of said granule.

13. The process of claim 12 wherein said plasticizer is selected from the group consisting of: polyols, urea, sugars, sugar alcohols, oxa diacids, diglycolic acids, linear carboxylic acids with at least one ether group, Cl-Cl$_2$ dialkyl phthalate, ethanolacetamide, ethanolformamide, tricthanolamines, thiocyanates, glycerol, rriethylene glycol, propylene glycol, sorbitol, and polyethylene glycol having an average molecular weight below about 600.

14. The process of claim 1 wherein said granule further comprises a water-dispersible polymer selected from the group consisting of polyvinyl alcohol, polyethylene glycol, polyethylene oxide, polyvinyl pyrrolidone, cellulose ether, and hydroxypropyl starch.

15. The process of claim 1 wherein said granule has a density of between 0.8 to 1.2 g/cm$^3$ and a diameter of between 0.01 and 0.5 millimeters.

16. The process of claim 1 wherein the foliage is blade grass.

17. The process of claim 1 wherein the foliage is horticultural crop.

18. The process of claim 1 wherein the foliage is an orchard crop.

\* \* \* \* \*